Figure 1:
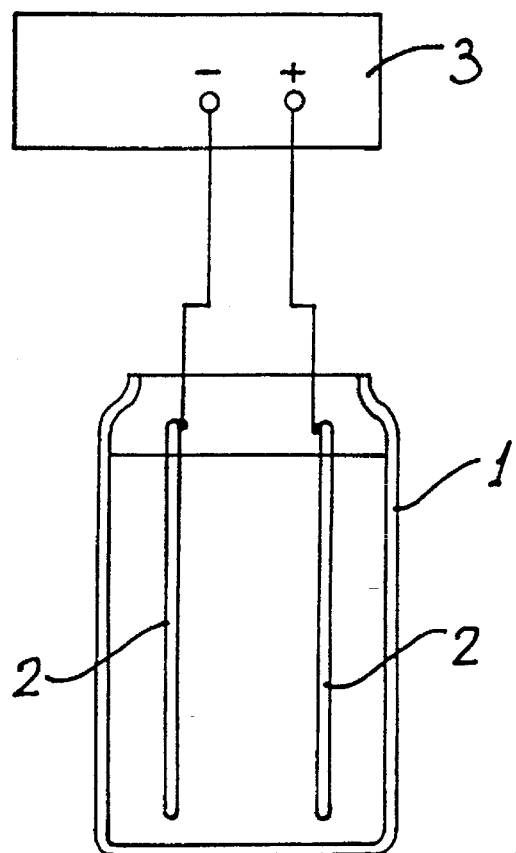

United States Patent [19]

Nelson et al.

[11] Patent Number: 5,603,915
[45] Date of Patent: Feb. 18, 1997

[54] PROCESS FOR MANUFACTURING HOMEOPATHIC MEDICINES

[76] Inventors: William Nelson, 6968 Buckskin Dr., Littleton, Colo. 80127; Carmel Kiely, 17 Russell Place, Dooradoyla, Limerick, Ireland

[21] Appl. No.: 215,720

[22] Filed: Mar. 22, 1994

[51] Int. Cl.$^6$ ............... A61K 51/00; C07C 1/00; H05F 3/00
[52] U.S. Cl. ............... 424/1.11; 204/157.15; 204/164
[58] Field of Search ............ 424/1.11; 204/157.15, 204/164, 186

[56] References Cited

FOREIGN PATENT DOCUMENTS 5930215  3/1993  Ireland ............ A61K 47/46

Primary Examiner—John W. Rollins

[57] ABSTRACT

A homeopathic medicine comprises a homeopathic carrier solution which is prepared by mixing a base solution of alcohol and water in the ratio of 1 part alcohol to 9 parts water, and subsequently mixing in sea water, brain hormone and biologically active enzymes into the base solution in the proportion 9x, 12x and 12x, respectively. The homeopathic carrier solution is sequentially subjected to an alternating current and a direct current treatment which requires applying an alternating current of 20 milliamps at 10 volts and 10 KHz for a duration of 30 seconds and a DC current of 20 milliamps at 1,000 volts for 4 minutes. The active homeopathic ingredient is then added to the carrier solution.

7 Claims, 1 Drawing Sheet

5,603,915

PROCESS FOR MANUFACTURING HOMEOPATHIC MEDICINES

FIELD OF THE INVENTION

The present invention relates to a method for preparing a homeopathic carrier solution for subsequent use in a homeopathic medicine for increasing the efficacy of the homeopathic medicine, and to a homeopathic carrier solution prepared according to the method. The invention also relates to a homeopathic medicine comprising the homeopathic carrier solution, and to a method for preparing the homeopathic medicine.

BACKGROUND TO THE INVENTION

Homeopathic medicines are well known, and in general, are manufactured using the Hahnemanian process. In general, the active homeopathic ingredient is dispersed in a carrier solution, generally, a solution of water and alcohol or an alkaloid mixture. Where the carrier solution is a water and alcohol base solution, the water is normally purified prior to mixing with the alcohol. The active homeopathic ingredient of the medicine is mixed with the carrier solution in the appropriate proportion to achieve the desired concentration of the active homeopathic ingredient in the carrier solution.

A 1× potency homeopathic medicine is a solution which comprises one part of active homeopathic ingredient to nine parts of carrier solution. A 2× potency homeopathic medicine is a solution which comprises one part of active homeopathic ingredient to ninety-nine parts of carrier solution. A 3× potency homeopathic solution is one which comprises one part active homeopathic ingredient to nine hundred and ninety-nine parts carrier solution. An N× potency homeopathic medicine is a solution of one part of active homeopathic ingredient to $(10^N-1)$ parts of carrier solution. In general, the appropriate proportions of active homeopathic ingredient and carrier solution are added to a container and the active homeopathic ingredient is dispersed through the carrier solution by succussing the container which requires striking the container on a blunt object one or more times.

OBJECTS OF THE INVENTION

One object of the invention is to provide a homeopathic carrier solution which when carrying an active ingredient in a homeopathic medicine significantly increases the efficacy of the homeopathic medicine. Another object of the invention is to provide a method for preparing such a homeopathic carrier solution. It is also an object of the invention to provide a homeopathic medicine with a relatively high efficacy, and in particular, an efficacy which is significantly improved over the efficacy of known homeopathic solutions. Additionally, it is an object of the invention to provide a method for providing such a homeopathic carrier solution.

It has been surprisingly found that the efficacy of a homeopathic medicine may be increased by subjecting the homeopathic carrier solution to electrical treatments prior to the addition of the active homeopathic ingredient. It has also been found that the efficacy of the homeopathic medicine can be improved by adding sea water, brain hormone and biologically active enzymes to the homeopathic carrier solution prior to adding the active homeopathic ingredient.

SUMMARY OF THE INVENTION

According to the invention there is provided a method for preparing a homeopathic carrier solution for increasing the efficacy of a homeopathic medicine comprising the carrier solution, the method comprising the steps of sequentially subjecting the homeopathic carrier solution to an alternating current electrical treatment and a direct current electrical treatment, the alternating current electrical treatment comprising the steps of subjecting the homeopathic carrier solution to an alternating current in the range of 1 milliamp to 100 milliamps at a potential in the range of 5 volts to 30 volts and at a frequency in the range of 1 KHz to 1,000 KHz for a duration in the range of 20 seconds to 60 seconds, the direct current electrical treatment comprising the steps of subjecting the homeopathic carrier solution to a direct current in the range of 1 milliamp to 50 milliamps at a potential of 500 volts to 10,000 volts for a duration not exceeding 5 minutes.

In one embodiment of the invention the alternating current electrical treatment comprises the steps of subjecting the homeopathic carrier solution to an alternating current in the range of 10 milliamps to 50 milliamps at a potential in the range of 5 volts to 15 volts and a frequency in the range of 5 KHz to 20 KHz for a duration in the range of 25 seconds to 35 seconds.

In another embodiment of the invention the direct current electrical treatment comprises the steps of subjecting the homeopathic carrier solution to a direct current in the range of 15 milliamps to 25 milliamps at a voltage in the range of 900 volts to 1,100 volts for a duration in the range 3 minutes to 5 minutes.

Additionally, the invention provides a homeopathic carrier solution treated according to the invention. Preferably, the homeopathic carrier solution further comprising any one or more of the following ingredients:
sea water,
brain hormones, and
biologically active enzymes.

Further the invention provides a homeopathic medicine comprising the homeopathic carrier solution of the invention.

Additionally, the invention provides a method for preparing a homeopathic medicine of N× potency, the method comprising the steps of preparing a 1× potency solution by adding one part of an active homeopathic ingredient and nine parts of the homeopathic carrier solution according to the invention to a container, and dispersing the active homeopathic ingredient through the homeopathic carrier solution by succussing the container by striking the container containing the active homeopathic ingredient and the homeopathic carrier solution on a blunt object, preparing a 2× potency solution by adding one part of the 1× potency solution and nine parts of the homeopathic carrier solution according to the invention to a container and dispersing the 1× potency solution through the homeopathic carrier solution by succussing the container containing the 1× potency solution and the homeopathic carrier solution by striking the container on a blunt object, and so on until an (N−1)× potency solution has been prepared, preparing the N× potency solution by adding one part of the (N−1)× potency solution and nine parts of the homeopathic carrier solution according to the invention to a container and dispersing the (N−1)× potency solution through the homeopathic carrier solution by succussing the container containing the (N−1)× potency solution and the homeopathic carrier solution by striking the container on a blunt object.

ADVANTAGES OF THE INVENTION

The advantages of the invention are many. As discussed below, it has been found by carrying out relatively extensive tests that the efficacy of a homeopathic medicine when prepared using the homeopathic carrier solution according to the invention is relatively high, and is significantly improved over known homeopathic medicines.

Figure 2:
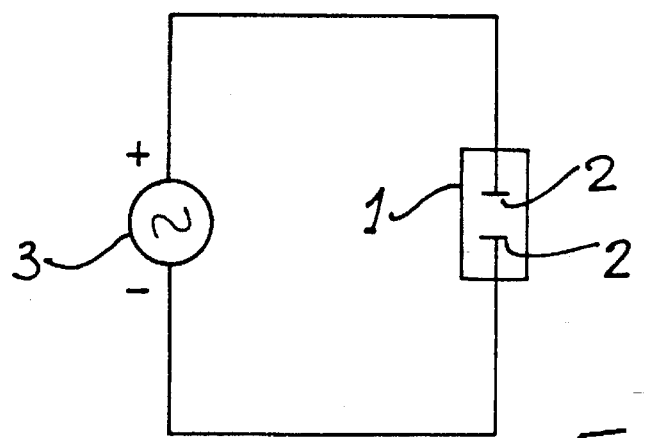

These and other advantages and objects of the invention will be more clearly understood from the following description of some preferred embodiments thereof which are given by way of example only, with reference to the accompanying drawings, in which:

FIG. 1 is a schematic representation of apparatus for carrying out the method of the invention, and FIG. 2 is a circuit diagram of the apparatus of FIG. 1.

In the preparation of a homeopathic medicine according to the invention a homeopathic carrier solution also according to the invention is prepared which includes one or more of the following ingredients,
sea water,
brain hormones, and
biologically active enzymes.

The homeopathic carrier is subjected to electrical treatments prior to the addition of the active homeopathic ingredient. An example of a homeopathic carrier solution according to the invention is described in the following example 1. Examples of homeopathic medicines according to the invention are described in examples 2 to 5.

EXAMPLE 1

A homeopathic carrier solution is prepared using a water and alcohol base solution prepared by mixing alcohol and purified water in the ratio of 1 part alcohol to 9 parts water by volume. The following ingredients are then added to the water and alcohol base solution in the proportion set out below by volume.
1 part sea water to $10^9$ parts base solution.
1 part brain hormone mixture to $10^{12}$ parts base solution.
1 part biologically active enzyme mixture to $10^{12}$ parts base solution.

The brain hormone mixture contains the following hormones:
endorphins, serotonin, neurotensin, somatostatin, enkephalin, neuropeptides, cholecystakinin, norepinephrine, gama amino benzoic acid, epinephrine, and dopamine.

The biologically active enzyme mixture contains the following ingredients:
DNA polymerase, RNA polymerase, protease, lipase, and amylase.

The water and alcohol base solution is poured into a container 1, see FIGS. 1 and 2 of the appropriate size and the sea water, brain hormone and biologically active enzymes are added to the water and alcohol base solution which is thoroughly mixed to prepare the homeopathic carrier solution. The carrier solution is then subjected to the electrical treatments using the following method and the apparatus illustrated in FIGS. 1 and 2. A pair of spaced apart electrodes 2 which are spaced apart a distance of 20 mm are placed in the carrier solution to a depth of 50 mm. Each electrode 2 is of 2 mm width, thereby providing an effective area of 100 mm² of each electrode immersed in the carrier solution. The output terminals of a function generator 3 illustrated in block representation are connected to the electrodes 2. The homeopathic carrier solution is subjected to two electrical treatments sequentially. The first treatment is an alternating current treatment, while the second treatment is a direct current treatment. In the alternating current treatment the function generator 3 is set to deliver an alternating current of approximately 20 milliamps at a potential of approximately 10 volts and at a frequency of approximately 10 KHz. The alternating current is applied to the electrodes 2 in the carrier solution for a duration of approximately 30 seconds. When the carrier solution has been subjected to the alternating current for 30 seconds the direct current treatment is immediately commenced. The function generator 3 is set to deliver a direct current to the electrodes 2 of approximately 20 milliamps at a potential of approximately 1,000 volts. The direct current is applied to the carrier solution for a duration of 4 minutes approximately, thereby creating a tachyon field through the homeopathic carrier solution.

To establish the improvement in efficacy of homeopathic medicines using the carrier solution of example 1, four homeopathic medicines including the carrier solution of example 1 were prepared, and comparative tests were carried out on human subjects as discussed below. The four homeopathic medicines were prepared according to the following examples 2 to 5.

EXAMPLE 2

A homeopathic medicine for use in the treatment of milk allergies was prepared from the following ingredients.
1 drop of a 3× potency of milk solution, and
1 ounce (approximately) of the carrier solution of example 1.

The 3× potency milk solution was prepared as follows.

A 1× solution of an active homeopathic ingredient, in this case milk, and the carrier solution of example 1 was prepared by adding one part of cow's milk to nine parts of the homeopathic carrier solution of example 1. The mixture was succussed by striking the container containing the mixture on a blunt object, in this case, a leather-bound book fifteen times to fully disperse the milk throughout the carrier solution. A 2× solution was then prepared from the 1× solution by mixing one part of the 1× solution with nine parts of the homeopathic carrier solution of example 1. This new mixture was succussed by striking the container containing the new mixture fifteen times on a leather-bound book to disperse the 1× solution throughout the homeopathic carrier solution, thereby forming a 2× solution. The 3× potency milk solution was prepared from the 2× solution. One part of the 2× solution was mixed with nine parts of the homeopathic carrier solution of example 1. The mixture of the 2× solution and the carrier solution was succussed by striking the container containing the mixture fifteen times on a leather-bound book to form the 3× potency milk solution.

The one drop of the 3× potency milk solution was added to a one ounce bottle, and the bottle was then filled with the homeopathic carrier solution of example 1. A dropper was placed on top of the bottle which was succussed by striking the bottle fifteen times on a leather-bound book, and the homeopathic medicine was ready for use.

EXAMPLE 3

A homeopathic medicine for use in the treatment of hypoadrenia was prepared from the following ingredients.
1 drop of a 3× potency adrenalin gland solution, and
1 ounce (approximately) of the homeopathic carrier solution of example 1.

The 3× potency adrenalin gland solution was prepared from liquidised animal adrenal glands mixed with the homeopathic carrier solution of example 1. A 1× solution of an active homeopathic ingredient, namely, the adrenal gland and the homeopathic carrier solution of example 1 was first prepared, from which a 2× potency was then prepared and subsequently a 3× potency was prepared using similar steps as those described for preparing the 3× potency milk solution of example 2.

One drop of the 3× potency adrenal gland solution was added to a one ounce bottle. The bottle was then filled with the homeopathic carrier solution of example 1. A dropper was placed on the bottle which is succussed by striking the bottle fifteen times on a leather-bound book and the homeopathic medicine was ready for use.

EXAMPLE 4

A homeopathic medicine for the treatment of environmental allergies was prepared from the following ingredients.

77 drops of a 3× potency solution of a blend of environmental detoxifying homeopathics, and 1 gallon (approximately) of the homeopathic solution of example 1.

The 3× potency solution of the blend of environmental isode detoxifying homeopathics was prepared in similar fashion as the 3× potency milk solution of example 2. Initially, an active homeopathic ingredient, namely, a blend of environmental detoxifying homeopathics was added to the carrier solution of example 1 in the ratio 1 part blend to 9 parts carrier solution by volume to form a 1× potency solution. 2× and 3× potency solutions were subsequently formed.

Seventy-seven drops of the 3× potency solution were added to a one gallon bottle. The bottle was then half filled with the homeopathic carrier solution of example 1, and the mixture was succussed by striking the bottle fifteen times on a leather-bound book. The bottle was then filled with the remainder of the homeopathic carrier solution of example 1 and again succussed by striking the bottle fifteen times on a leather-bound book and the homeopathic medicine was ready for use.

EXAMPLE 5

A homeopathic medicine for use in the treatment of bacterial infections was prepared from the following ingredients:

77 drops of a 3× potency solution of a blend of bacterial detoxifying homeopathics, and 1 gallon (approximately) of the homeopathic carrier solution of example 1.

The 3× potency solution of the blend of bacterial detoxifying homeopathics was prepared in similar fashion as the 3× potency milk solution of example 2.

Initially, an active homeopathic ingredient, namely, a blend of bacterial detoxifying nozode homeopathics was added to the carrier solution of example 1 in the ratio 1 part blend to 9 parts carrier solution by volume to form a 1× potency solution. 2× and 3× potency solutions were subsequently formed.

Seventy-seven drops of the 3× potency solution was added to a one gallon bottle. The one gallon bottle was then half filled with the homeopathic carrier solution of example 1 and the bottle was succussed by striking the bottle fifteen times on a leather-bound book. The bottle was then filled with the remainder of the homeopathic carrier solution of example 1 and the bottle was again succussed by striking the bottle fifteen times on a leather-bound book. The homeopathic medicine was then ready for use.

Four homeopathic medicines prepared using identical active homeopathic ingredients, namely, cow's milk, adrenal glands, a blend of environmental detoxifying homeopathics, and a blend of bacterial detoxifying homeopathics, respectively, but with conventional carrier solutions were prepared for use as reference homeopathic medicines in the tests on the human subjects. The proportion of the active homeopathic ingredients in each reference homeopathic medicine was identical to that in the corresponding homeopathic medicines of examples 2 to 5. The carrier solution used in the reference homeopathic medicines was a mixture of purified water and 200 proof alcohol which was mixed with the water in the ratio one part alcohol to nine parts purified water by volume. The carrier solution contained no other additives and was not subjected to any electrical treatment.

For convenience the homeopathic medicines of examples 2 to 5 will be referred to as the test homeopathic medicines and the homeopathic medicines made using the conventional carrier solution will be referred to as the reference homeopathic medicines.

Tests

Four sets of comparative tests were carried out for the respective test homeopathic medicines. In each set of tests a group of twenty human subjects which presented with an appropriate condition were selected. In each group ten of the twenty subjects were treated with the appropriate test homeopathic medicine and ten of the group were treated with the corresponding reference homeopathic medicine. The subjects were randomly selected for treatment with the respective test and reference homeopathic medicines. The results of the tests are as follows:

Test 1

In this test twenty subjects who presented with an allergy to cow's milk were treated. Ten of the subjects S1 to S10 were randomly selected and treated with the test homeopathic medicine prepared in example 2 and the other ten subjects, namely, subjects S11 to S20 were treated with the reference homeopathic medicine.

TABLE 1

| Test homeopathic medicine | | Reference homeopathic medicine | |
| --- | --- | --- | --- |
| Subject | Cure Time (weeks) | Subject | Cure time (weeks) |
| S1 | 3 | S11 | 8 |
| S2 | 6 | S12 | 10 |
| S3 | 7 | S13 | 12 |
| S4 | 10 | S14 | 9 |
| S5 | 4 | S15 | 7 |
| S6 | 7 | S16 | 12 |
| S7 | 6 | S17 | 10 |
| S8 | 8 | S18 | 8 |
| S9 | 8 | S19 | 7 |
| S10 | 5 | S20 | 6 |
| Average Cure Time | 6.4 | Average Cure Time | 8.9 |

Each subject was treated until his or her sensitivity to cow's milk was reduced to a level where the allergy could be considered to be cured. The treatment regime was as follows, one drop of the homeopathic medicine was administered orally to the subject three times per day under the tongue of the subject. The reduction in each subjects sensitivity to milk was monitored on a weekly basis as follows. At the end of each week of the treatment each subject consumed 5 mL of cow's milk and their reaction to the milk was monitored. In all cases after varying periods of treatment the subjects being treated with the test homeopathic medicine and the subjects being treated with the reference homeopathic medicine were cured. The results of the tests are set out in Table 1 which shows the cure time for each subject in weeks. The average cure time for the subjects S1 to S10 who had been treated with the test homeopathic medicine was 6.4 weeks, which was considerably less than the average cure time of 8.9 weeks for the subjects S11 to S20 who had been treated with the reference homeopathic medicine.

Test 2

Twenty subjects which presented with hypoadrenia were randomly divided into two groups of ten, namely, subjects S1 to S10 and subjects S11 to S20. The subjects S1 to S10 were treated with the test homeopathic medicine of example 3 and the subjects S11 to S20 were treated with the reference homeopathic medicine which corresponded to the test homeopathic medicine. The treatment regime for each subject was

TABLE 2

| Test homeopathic medicine | | Reference homeopathic medicine | |
| --- | --- | --- | --- |
| Subject | Cure Time (weeks) | Subject | Cure time (weeks) |
| S1 | 4 | S11 | 4 |
| S2 | 4 | S12 | 5 |
| S3 | 3 | S13 | 6 |
| S4 | 2 | S14 | 3 |
| S5 | 1 | S15 | 2 |
| S6 | 2 | S16 | 2 |
| S7 | 4 | S17 | 4 |
| S8 | 2 | S18 | 3 |
| S9 | 1 | S19 | 2 |
| S10 | 3 | S20 | 6 |
| Average Cure Time | 2.6 | Average Cure Time | 3.7 | as follows. One drop of homeopathic medicine was administered three times per day orally under the tongue. The progress of the subjects was monitored on a weekly basis. At the end of each week of treatment the subjects progress was monitored by taking the ortho-static blood pressure of each subject. The treatment of each subject continued until his/her blood pressure was at a level which indicated that the hypoadrenia had been cured. In all cases after varying periods of treatment the subjects being treated with the test homeopathic medicine and the subjects being treated with reference homeopathic medicine were cured. The results of the tests are set out in table 1 which shows the cure time for each subject in weeks. The average cure time for the subjects S1 to S10 who had been treated with the test homeopathic medicine was 2.6 weeks, which was considerably less than the average cure time of 3.7 weeks for the subjects S11 to S20 who had been treated with the reference homeopathic medicine.

Test 3

Twenty subjects which presented with various environmental allergies were randomly divided into two groups of ten, namely, subjects S1 to S10 and subjects S11 to S20. The subjects S1 to S10 were treated with the test homeopathic medicine of example 4 and the subjects S11 to S20 were treated with the reference homeopathic medicine corresponding to the test homeopathic medicine of example 4. The treatment regime was as follows, one drop of homeopathic medicine was administered orally three times per day to each subject under the tongue. The treatment of each subject was continued until the allergy was cured. The subjects progress was monitored weekly.

At the end of each week each subject's sensitivity to the environmental allergy was monitored. The results of the tests are set out in Table 3. In all cases

TABLE 3

| Test homeopathic medicine | | Reference homeopathic medicine | |
| --- | --- | --- | --- |
| Subject | Cure Time (weeks) | Subject | Cure time (weeks) |
| S1 | 4 | S11 | 3 |
| S2 | 5 | S12 | 5 |
| S3 | 3 | S13 | 10 |
| S4 | 2 | S14 | 5 |
| S5 | 1 | S15 | 10 |
| S6 | 2 | S16 | 6 |
| S7 | 3 | S17 | 3 |
| S8 | 8 | S18 | 10 |
| S9 | 2 | S19 | 6 |
| S10 | 3 | S20 | 4 |
| Average Cure Time | 3.3 | Average Cure Time | 6.2 | after varying periods of treatment the subjects being treated with the test homeopathic medicine and the subjects being treated with reference homeopathic medicine were cured. The results of the tests are set out in table 1 which shows the cure time for each subject in weeks. The average cure time for the subjects S1 to S10 who had been treated with the test homeopathic medicine was 3.3 weeks, which was considerably less than the average cure time of 6.2 weeks for the subjects S11 to S20 who had been treated with the reference homeopathic medicine.

Test 4

Twenty subjects which presented with bacterial urinary infection were randomly divided into two groups of ten, namely, subjects S1 to S10 and subjects S11 to S20. The subjects S1 to S10 were treated with the test homeopathic medicine of example 5 while the subjects S11 to S20 were treated with the reference homeopathic medicine corresponding to the test homeopathic medicine of example 5. The treatment regime for all twenty subjects was as follows, one drop of the homeopathic medicine was administered orally to each subject three times per day under the tongue. The subjects' progress were monitored on a weekly basis. Treatment continued until the bacterial urinary infection in each subject was cured. A cure was determined when all symptoms of the bacterial urinary infection disappeared. The results of the tests are set out in Table 4. In all cases after varying periods of treatment the subjects being treated with the test homeopathic medicine and the subjects being treated with reference homeopathic medicine were cured. The results of the tests are set out in table 1 which shows the cure time for each subject in weeks. The average cure time for the subjects S1 to S10 who had been treated with the test homeopathic medicine was 3.1 weeks, which was considerably less than the average cure time of 5.5

TABLE 4

| Test homeopathic medicine | | Reference homeopathic medicine | |
|---|---|---|---|
| Subject | Cure Time (weeks) | Subject | Cure time (weeks) |
| S1 | 3 | S11 | 5 |
| S2 | 2 | S12 | 6 |
| S3 | 3 | S13 | 7 |
| S4 | 4 | S14 | 7 |
| S5 | 3 | S15 | 6 |
| S6 | 2 | S16 | 5 |
| S7 | 4 | S17 | 4 |
| S8 | 5 | S18 | 4 |
| S9 | 3 | S19 | 5 |
| S10 | 2 | S20 | 6 |
| Average Cure Time | 3.1 | Average Cure Time | 5.5 | weeks for the subjects S11 to S20 who had been treated with the reference homeopathic medicine.

Accordingly, it has been demonstrated that the preparation of homeopathic medicines using the homeopathic carrier solution according to the invention considerably improves the efficacy of the homeopathic medicine.

While the active homeopathic ingredient of the homeopathic medicines, namely, cow's milk, adrenalin glands, a blend of environmental detoxifying homeopathics, and a blend of bacterial detoxifying homeopathics have not been described in detail, such active homeopathic ingredients will be well known to those skilled in the art of homeopathic medicines.

It will of course be appreciated that homeopathic medicines with other active homeopathic ingredients may be prepared using the homeopathic carrier solution according to the invention. While a specific homeopathic carrier solution has been described in example 1, this example is not to be considered in any way as limiting the scope of the invention.

We claim:

1. A method for preparing a homeopathic carrier solution for increasing the efficacy of a homeopathic medicine comprising the carrier solution, the method comprising the steps of sequentially subjecting the homeopathic carrier solution to an alternating current electrical treatment and a direct current electrical treatment, the alternating current electrical treatment comprising the steps of subjecting the homeopathic carrier solution to an alternating current in the range of 1 milliamp to 100 milliamps at a potential in the range of 5 volts to 30 volts and at a frequency in the range of 1 KHz to 1,000 KHz for a duration in the range of 20 seconds to 60 seconds, the direct current electrical treatment comprising the steps of subjecting the homeopathic carrier solution to a direct current in the range of 1 milliamp to 50 milliamps at a potential of 500 volts to 10,000 volts for a duration not exceeding 5 minutes.

2. A method as claimed in claim 1 in which the alternating current electrical treatment comprises the steps of subjecting the homeopathic carrier solution to an alternating current in the range of 10 milliamps to 50 milliamps at a potential in the range of 5 volts to 15 volts and a frequency in the range of 5 KHz to 20 KHz for a duration in the range of 25 seconds to 35 seconds.

3. A method as claimed in claim 1 in which the direct current electrical treatment comprises the steps of subjecting the homeopathic carrier solution to a direct current in the range of 15 milliamps to 25 milliamps at a voltage in the range of 900 volts to 1,100 volts for a duration in the range 3 minutes to 5 minutes.

4. The homeopathic carrier solution prepared by the electrical activation method of claim 1.

5. A homeopathic carrier solution as claimed in claim 4 in which the homeopathic carrier solution further comprises any one or more of the following ingredients:

sea water, brain hormones, and biologically active enzymes.

6. A method for preparing a homeopathic medicine of N× potency, the method comprising the steps of preparing a 1× potency solution by adding one part of an active homeopathic ingredient and nine parts of the electrically treated homeopathic carrier solution are added to a container, and dispersing the active homeopathic ingredient through the homeopathic carrier solution by succussing the container by striking the container containing the active homeopathic ingredient and the homeopathic carrier solution on a blunt object, preparing a 2× potency solution by adding one part of the 1× potency solution and nine parts of the homeopathic carrier solution as claimed in claim 4 to a container and dispersing the 1× potency solution through the homeopathic carrier solution by succussing the container containing the 1× potency solution and the homeopathic carrier solution by striking the container on a blunt object, and so on until an (N–1)× potency solution has been prepared, preparing the N× potency solution by adding one part of the (N–1)× potency solution and nine parts of the electrically treated homeopathic carrier solution are added to a container and dispersing the (N–1)× potency solution through the homeopathic carrier solution by succussing the container containing the (N–1)× potency solution and the homeopathic carrier solution by striking the container on a blunt object.

7. A homeopathic medicine composition comprising a homeopathic medicine and the homeopathic carrier solution as claimed in claim 4.

* * * * *